US008491940B2

(12) United States Patent
Remington et al.

(10) Patent No.: US 8,491,940 B2
(45) Date of Patent: Jul. 23, 2013

(54) PETROLEUM-FREE COMPOSITIONS FOR SKIN CARE AND OTHER APPLICATIONS, AND METHODS OF MAKING SAME

(75) Inventors: Chris Ejyo Remington, San Francisco, CA (US); Todd Stuart Cooper, San Francisco, CA (US)

(73) Assignee: Waxelene, Inc., San Francisco, CA (US)

( * ) Notice: Subject to any disclaimer, the term of this patent is extended or adjusted under 35 U.S.C. 154(b) by 0 days.

(21) Appl. No.: 13/077,549

(22) Filed: Mar. 31, 2011

(65) Prior Publication Data

US 2012/0076867 A1 Mar. 29, 2012

Related U.S. Application Data

(62) Division of application No. 13/074,611, filed on Mar. 29, 2011.

(60) Provisional application No. 61/395,441, filed on May 12, 2010.

(51) Int. Cl.
| | |
|---|---|
| *A61K 36/00* | (2006.01) |
| *A61K 36/889* | (2006.01) |
| *A61K 36/736* | (2006.01) |
| *A61K 36/87* | (2006.01) |
| *A61K 36/48* | (2006.01) |
| *A61K 36/55* | (2006.01) |

(52) U.S. Cl.
USPC ........... 424/725; 424/757; 424/727; 424/766; 424/768; 424/764

(58) Field of Classification Search
None
See application file for complete search history.

(56) References Cited

U.S. PATENT DOCUMENTS

| | | | | |
|---|---|---|---|---|
| 1,854,237 | A | * | 4/1932 | Teeple .......................... 508/116 |
| 2,891,864 | A | * | 6/1959 | Baxter ............................ 426/72 |
| 2,982,691 | A | * | 5/1961 | Winsten ......................... 424/489 |
| 4,665,100 | A | * | 5/1987 | Ludwig .......................... 514/778 |
| 5,650,185 | A | | 7/1997 | Stoltz |
| 5,723,137 | A | | 3/1998 | Wahle et al. |
| 6,348,229 | B1 | | 2/2002 | Eini et al. |
| 6,500,440 | B1 | | 12/2002 | Chi et al. |
| 6,503,944 | B1 | | 1/2003 | Chanchani |
| 6,506,397 | B1 | | 1/2003 | Thies |
| 6,699,487 | B2 | | 3/2004 | Ito et al. |
| 6,792,701 | B1 | | 9/2004 | Ruffini et al. |
| 7,060,306 | B2 | | 6/2006 | Springstead |
| 7,273,622 | B2 | | 9/2007 | Udell et al. |
| 7,399,492 | B2 | | 7/2008 | Xu |
| 7,674,848 | B2 | | 3/2010 | Lin |
| 7,691,419 | B2 | | 4/2010 | DiLeva |
| 7,708,822 | B2 | | 5/2010 | Lahav et al. |
| 2002/0098989 | A1 | * | 7/2002 | Heimann et al. .............. 508/136 |
| 2004/0018250 | A1 | | 1/2004 | Ceccoli et al. |
| 2006/0089274 | A1 | * | 4/2006 | Sarkis et al. .................. 508/390 |
| 2006/0107870 | A1 | | 5/2006 | Barnes |
| 2007/0286826 | A1 | | 12/2007 | Grune |
| 2008/0233060 | A1 | | 9/2008 | Grune |
| 2009/0162304 | A1 | | 6/2009 | DiLeva |
| 2009/0217568 | A1 | | 9/2009 | Murphy et al. |
| 2011/0280969 | A1 | | 11/2011 | Remington et al. |

FOREIGN PATENT DOCUMENTS

JP 10313797 A * 12/1998

OTHER PUBLICATIONS

Anonymous, Sieve unit reduceds process time for lubricants, Filtration + Separation (2007), 44 (3), 10.*

* cited by examiner

*Primary Examiner* — Qiuwen Mi
(74) *Attorney, Agent, or Firm* — Sterne, Kessler, Goldstein & Fox P.L.L.C.

(57) ABSTRACT

A substantially non-aqueous, aerated composition is free of petroleum-based components and is suitable for skin applications. The composition primarily includes wax and oil, and can further include vitamin E oil and an essential oil. The composition can be a semi-solid at room temperature. A method of making the composition includes melting together component ingredients to form a mixture, which is then cooled to form hardened matter. The hardened matter is blended to form a flowable mixture, which is then forced through a sieve to form the aerated composition.

24 Claims, 1 Drawing Sheet

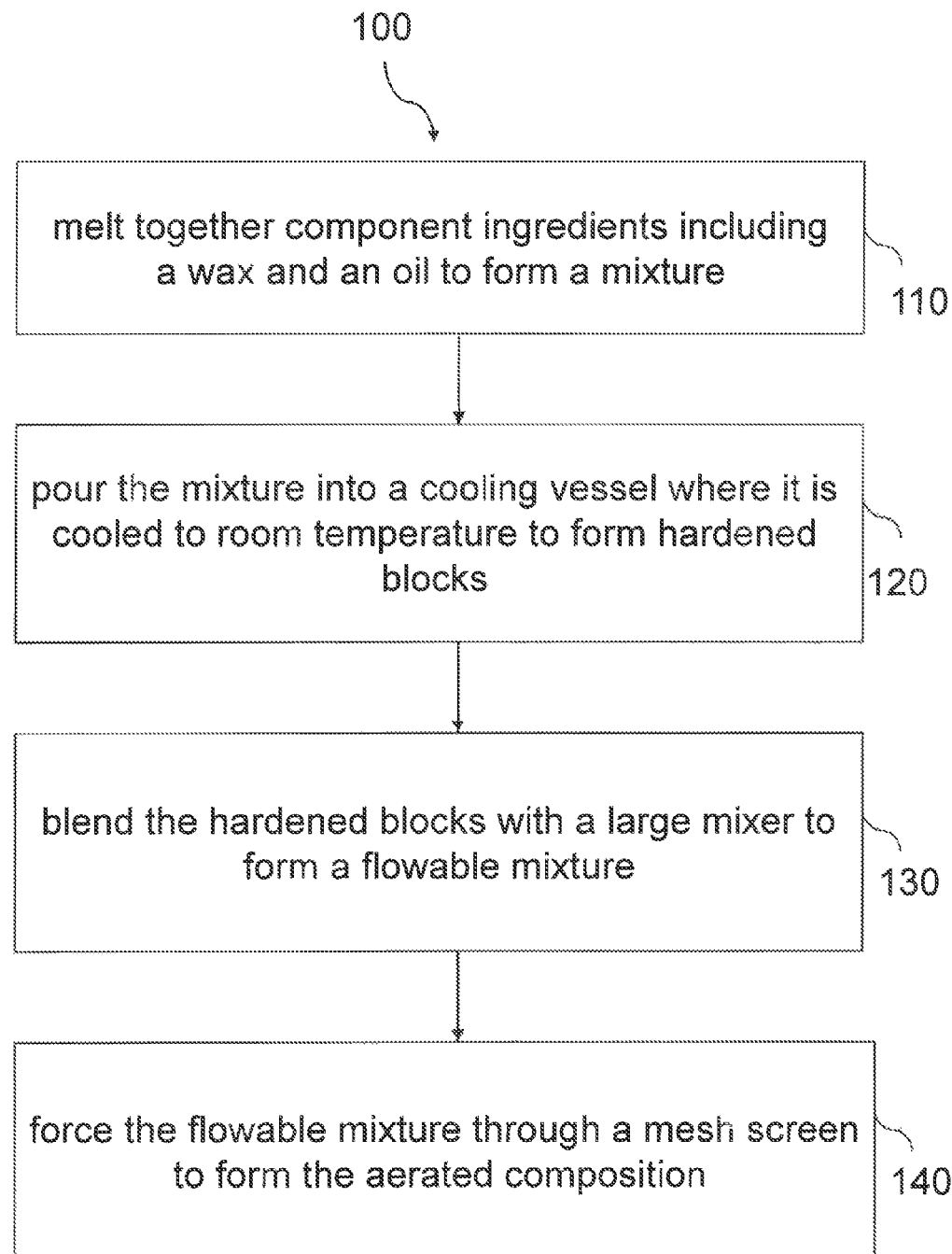

PETROLEUM-FREE COMPOSITIONS FOR SKIN CARE AND OTHER APPLICATIONS, AND METHODS OF MAKING SAME

CROSS-REFERENCE TO RELATED APPLICATION

This application is a divisional of U.S. application Ser. No. 13/074,611, filed Mar. 29, 2011, which claims the benefit of U.S. Provisional Application No. 61/395,441 filed May 12, 2010, the entire disclosures of which are incorporated herein by reference thereto.

BACKGROUND OF THE INVENTION

1. Field of the Invention

The present invention relates to lubricants, such as topical lubricants for application to the skin, and in particular to substantially non-aqueous, aerated compositions which are primarily made of wax and oil, are suitable for skin applications, and are free of petroleum-based components.

2. Background

Many lubricants contain petroleum jelly. Petroleum jelly, or petrolatum, has long been employed in a variety of commercial, household, manufacturing and topical uses. Commercial uses include lip balm, candles, cosmetics, and lotions. Manufacturing uses include rust prevention and use as a release agent for plaster molds and castings. Household uses include removal of water rings from wood, soft leather, shine shoes and repair a squeaky door. Topical uses include, but are not limited to, preventing diaper rash, makeup removal and skin moisturizer.

Several long term side effects of petroleum-based chemicals, including petroleum jelly, have been observed. Petroleum-based chemicals are being found to cause significant attritional effects to the nervous system and immune system after prolonged exposure. Illnesses include cancer, neurological disorders, immune system weakening, autoimmune disorders, asthma, allergies, infertility, miscarriage, and child behavior disorders including learning disabilities, mental imparities, hyperactivity and attention deficit disorders (ADD). Petroleum-based chemicals are believed to cause these problems by a variety of routes including, but not limited to, impairment of gene expression, weakening of DNA repair mechanism, acceleration of gene loss, degeneration of the body's detoxification defense system (liver and kidneys), as well as gradual weakening of the brain's primary defense, the blood brain barrier (BBB).

In addition, petroleum-free products that seek to serve as a substitute for petroleum-based products like petroleum jelly may have a drawback of not having the same consistency or feel to the user in application as the petroleum-based products. For example, petroleum-free oil-based products which may be used as an alternative to petroleum jelly may have lower viscosity than conventional petroleum jelly, or the oil base may have been processed, e.g., by hydrogenation of the oil component, to provide a hydrogenated oil component having a thicker consistency than its non-hydrogenated counterpart.

Accordingly, there is a need for natural lubricants that are free of petroleum-based components and processes of preparing such lubricants. There is also a need for a natural lubricant to have a similar consistency as a petroleum-based product for which the natural lubricant may be an alternative, without requiring chemical alteration of the natural ingredients (e.g., via hydrogenation) to achieve this goal. The present application satisfies these and other needs, and provides further related advantages, as will be made apparent by the description of the embodiments that follow.

BRIEF SUMMARY OF THE INVENTION

Presented herein are substantially non-aqueous, aerated compositions that are free of petroleum-based components, and processes of preparing such compositions. In some embodiments, the compositions are also free of hydrogenated components. The compositions can be formulated for topical administration, preferably as topical lubricants, and in some embodiments, can serve as substitutes for conventional petroleum-based products, such as petroleum jelly, for example.

In some embodiments, a substantially non-aqueous, aerated composition includes a wax, an oil, vitamin E oil and an essential oil. In some embodiments, the wax can be present at a concentration from about 15 wt % to about 40 wt %, the oil can be present at a concentration from about 60 wt % to about 85 wt %, the vitamin E oil can be present at a concentration from about 0.01 wt % to about 10 wt %, and the essential oil can be present at a concentration from about 0.001 wt % to about 1 wt %.

In some embodiments, the composition is essentially made of beeswax, soybean oil, vitamin E oil, and an essential oil. The amount of beeswax is from about 15 wt % to about 40 wt % of the composition. The amount of soybean oil is from about 60 wt % to about 85 wt % of the composition. The amount of vitamin E oil is from about 0.01 wt % to about 10 wt % of the composition, and the amount of essential oil is from about 0.001 wt % to about 1 wt % of the composition. The composition is free of petroleum-based components, and is a semi-solid at a temperature of about 72° F. In some embodiments, the composition is the semi-solid and is also free of hydrogenated components.

In some embodiments, the wax can be animal tallow, bayberry wax, beeswax, candelilla wax, carnauba wax, grapefruit wax, montan wax, orange peel wax, palm wax, rice bran wax, sumac wax, sunflower wax, soy wax, or a mixture thereof. In some embodiments, the wax is beeswax. In some embodiments, the wax can have a melting point of from about 130° F. to about 160° F.

In some embodiments, the oil can be almond oil, babassu kernel oil, carrot seed oil, cashew oil, castor oil, coconut oil, cottonseed oil, corn oil, grape seed oil, hazelnut oil, linseed oil, macadamia oil, mongongo nut oil, olive oil, palm oil, palm kernel oil, peanut oil, pecan oil, pine nut oil, pistachio oil, pumpkin seed oil, rapeseed oil, safflower oil, sesame oil, soybean oil, sunflower oil, vegetable oil, walnut oil, or a mixture thereof. In some embodiments, the oil is soybean oil. In some embodiments, the oil is soybean oil and the wax is beeswax. In some embodiments, all or a portion of at least one of the soybean oil and the beeswax is substituted by one or more of carnauba wax, coconut oil, olive oil, soy wax, vegetable oil.

In some embodiments, the essential oil can be calendula, cedar, chamomiles, dove, cypress, geranium, jasmine, lavender, lemongrass, orange blossom, rose, rosemary, rosewood, peppermint, sandalwood, thyme, turmeric, or a mixture thereof. In some embodiments, the essential oil is rosemary oil.

Also presented herein are processes for preparing substantially non-aqueous, aerated compositions. In some embodiments, the process includes melting together components including a wax and an oil to form a mixture, pouring the mixture into a cooling vessel where it is cooled completely to room temperature to form hardened matter, blending the hardened matter with a mixer to form a flowable mixture, and forcing the flowable mixture through a sieve to form the aerated composition. In some embodiments, vitamin E oil and/or aloe vera extract, and in some embodiments, an essential oil, are melted together with the wax and the oil.

In some embodiments, a substantially non-aqueous, aerated composition can be prepared by (i) melting together (a) from about 15 wt % to about 40 wt % of a wax which is animal tallow, bayberry wax, beeswax, candelilla wax, carnauba wax, grapefruit wax, montan wax, orange peel wax, rice bran wax, sumac wax, sunflower wax, soy wax, or a mixture thereof, (b) from about 60 wt % to about 85 wt % of an oil which is almond oil, babassu kernel oil, carrot seed oil, cashew oil, castor oil, coconut oil, cottonseed oil, corn oil, grape seed oil, hazelnut oil, linseed oil, macadamia oil, mongongo nut oil, olive oil, palm oil, palm kernel oil, peanut oil, pecan oil, pine nut oil, pistachio oil, pumpkin seed oil, rapeseed oil, safflower oil, sesame oil, soybean oil, sunflower oil, vegetable oil, walnut oil, or a mixture thereof, (c) optionally, from about 0.01 wt % to about 10 wt % vitamin E oil, and (d) optionally, from about 0.001 wt % to about 1 wt % of an essential oil; (ii) pouring the mixture into a cooling vessel where it is cooled completely to room temperature to form hardened matter; (iii) blending the hardened matter with a mixer to thrill a flowable mixture; and (iv) forcing the flowable mixture through a sieve to form the aerated composition.

BRIEF DESCRIPTION OF THE DRAWING

The accompanying drawing, which is incorporated herein and forms a part of the specification, illustrates the present invention by way of example, and not by way of limitation. The drawing together with the description, further serves to explain the principles of the invention and to enable a person skilled in the pertinent art to make and use the invention.

FIG. 1 is a flowchart of an exemplary process for producing a substantially non-aqueous, aerated composition, according to embodiments described herein.

DETAILED DESCRIPTION OF THE INVENTION

Unless defined otherwise, all technical and scientific terms used herein have the same meanings as commonly understood by one of ordinary skill in the art to which this invention belongs. Although any processes and materials similar or equivalent to those described herein can be used in the practice of the present invention, the preferred compositions, materials and processes are described hereinafter. It will be apparent to a person skilled in the pertinent art that this invention can also be employed in a variety of other applications.

In order to further define this invention, the following terms and definitions are herein provided.

As used herein when referring to any numerical value, the term "about" means a value of ±10% of the stated value (e.g., "about 50° C." encompasses a range of temperatures from 45° C. to 55° C., inclusive).

As used herein, the term "cP" refers to a centipoise. A centipoise is a measure of the viscosity of a material, and is one one-hundredth of a poise, or one millipascal-second (mPa·s).

As used herein, the terms "disease" or "disorder" refer to any adverse condition of a human or animal including tumors, cancer, allergies, addiction, autoimmunity, infection, poisoning or impairment of optimal mental or bodily function.

"Conditions" as used herein includes diseases and disorders. Other conditions encompassed by the use of that term herein will be understood by those of ordinary skill in the art.

When the terms "one," "a," or "an" are used in this disclosure, they mean "at least one" or "one or more," unless otherwise indicated. As such, the terms "a" (or "an"), "one or more," and "at least one" can be used interchangeably herein.

As used herein, the term "semi-solid" refers to a composition that is intermediate in properties, especially in rigidity, between a solid and a liquid. A "semi-solid" composition can have a high viscosity and a relatively firm consistency compared to a liquid. Semi-solid compositions can include, for example, balms, pastes, creams, ointments, gels and lotions. Other semi-solid compositions will be understood by those of ordinary skill in the art.

As used herein, the terms "treatment," "treat," "treated" or "treating" refer to prophylaxis and/or therapy, particularly wherein the object is to prevent or slow down (lessen) an undesired physiological change or disorder. Alleviation can occur prior to signs or symptoms of disease appearing, as well as after their appearance. Thus, "treat", "treating" or "treatment" includes "prevent", "preventing" or "prevention" of the disease. In addition, "treat", "treating" or "treatment" does not require complete alleviation of signs or symptoms, does not require a cure, and specifically includes protocols which have only a marginal effect on the individual.

Compositions

Presented herein are substantially non-aqueous, aerated compositions that primarily include a wax and an oil and are free of petroleum-based components. In some embodiments, the compositions can also be semi-solid at room temperature and free of hydrogenated components. In some embodiments, an exemplary substantially non-aqueous, aerated composition includes a wax, an oil, optionally vitamin E oil, and optionally an essential oil.

Within the context of the present invention, the composition is a substantially non-aqueous preparation, which will be understood by those of skill in the art, to mean that it is anhydrous in that water has not been added as a component. However, those of skill in the art will also appreciate that water may be present in the composition via its presence in the formulation components and absorption from the atmosphere.

The wax component of the composition can provide a crystalline structure which gives the compositions rigidity and structure. In addition, the wax component can be impenetrable to water and upon application forms a waterproof barrier to prevent escape of water. The wax component can be a solid at room temperature (about 25° C. or about 72° F.). In some embodiments, the wax can have a melting point of from about 130° F. to about 160° F. Acceptable waxes include natural waxes and synthetic waxes. Suitable waxes include mono, di, and tri esters of saturated $C_{18}$-$C_{40}$ fatty acids with $C_{1-40}$ alcohols, and ester and alcohol derivatives of straight and branched chain fatty acids that are solid at room temperature (e.g., cetyl and stearyl alcohol, glyceryl dilaurate, and trihydroxystearin). Synthetic waxes include, but are not limited to, Fisher-Tropsch waxes, microcrystalline waxes, ethylene glycol diesters, triglyceride waxes, ethylene/vinylacetate copolymers, or a mixture thereof.

In some embodiments, the wax component of the composition can be animal tallow, bayberry wax, beeswax, candelilla wax, carnauba wax, grapefruit wax, montan wax, orange peel wax, palm wax, rice bran wax, sumac wax, sunflower wax, soy wax, or a mixture thereof. In some embodiments, the wax component is beeswax. Beeswax is a product from a bee hive, specifically the hive of any species of honey bee (the genus *Apis*).

In some embodiments, an amount of the wax component can be from about 15 wt % to about 30 wt %, from about 15 wt % to about 40 wt %, from about 20 wt % to about 35 wt %, and from about 20 wt % to about 40 wt %, for example.

The oil component of the composition can include one or more natural and/or synthetic oils, including by way of example and not limitation, vegetable oils, nut oils, and seed oils. As used herein, the term "oil" does not include vitamin E oil or essential oils. Vegetable oils are substances derived from plants that are composed of triglycerides. The oils are extracted from vegetables by chemical extraction or physical extraction methods and purified. Examples of vegetable oils include, but are not limited, to soybean oil, corn oil, and sunflower oil. In some embodiments, the oil component has not been subjected to a hydrogenation process, and as such, the oil component is not a hydrogenated (including partially hydrogenated) component.

In some embodiments, the oil component can be almond oil, babassu kernel oil, carrot seed oil, cashew oil, castor oil, coconut oil, cottonseed oil, corn oil, grape seed oil, hazelnut oil, linseed oil, macadamia oil, mongongo nut oil, olive oil, palm oil, palm kernel oil, peanut oil, pecan oil, pine nut oil, pistachio oil, pumpkin seed oil, rapeseed oil, safflower oil, sesame oil, soybean oil, sunflower oil, vegetable oil, walnut oil, or a mixture thereof. In some embodiments, the oil component is soybean oil.

In some embodiments, the oil component is soybean oil and the wax is beeswax, and in some embodiments, all or a portion of the soybean oil and/or the beeswax is substituted by one or more other components, such as by substituting the soybean oil and/or the beeswax with one or more of carnauba wax, coconut oil, olive oil, soy wax, and vegetable oil. In some embodiments, an amount of the oil component can be from about 60 wt % to about 85 wt % of the composition, and in some embodiments, about 74.9 wt % of the composition.

In some embodiments, the composition can include vitamin E oil. An amount of the vitamin E oil component of composition can be from about 0.01 wt % to about 10 wt % of the composition, and in some embodiments, about 0.135 wt % of the composition. As used herein, the term "vitamin E oil," which is also known as tocopherol, refers to a series of organic compounds that include methylated phenols and derivatives thereof. Vitamin E is a fat-soluble antioxidant that is known to promote healing of skin wounds. Sources of vitamin E oil include natural and synthetic sources. Natural sources include, but are not limited to, aloe vera, asparagus, avocados, broccoli, olives, mangoes, nuts, papayas, seeds and soybeans. An example of synthetically sourced vitamin E oil is vitamin E acetate. In some embodiments, the vitamin E oil component can from one or more of natural and synthetic sources, and can be any of alpha, beta, gamma, or delta tocopherols, or any mixture thereof, for example. In some embodiments, for example, the vitamin E oil component can be a mixture of alpha and beta tocopherols.

In some embodiments, aloe vera serves as the source of all or a portion of the vitamin B oil component, and in some embodiments, aloe vera extract is included in the composition. For example, in some embodiments, all or a portion of the vitamin E oil component is substituted with aloe vera extract. As used herein, "aloe vera extract" refers to the transparent gel from the pulp of the meaty leaves of aloe vera plant. Aloe vera extract has been used topically for thousands of years to beat wounds, skin infections, burns, and numerous other dermatologic conditions. Many of aloe vera extract's beneficial properties may be attributed to polysaccharides such as glucomannan and acemannan. In some embodiments, suitable aloe vera extract may be used either in water or oil-based liquid forms. In other embodiments, water may be added to oil-based aloe liquid to adjust the oiliness of the liquid.

In some embodiments, the composition can include an essential oil. An amount of the essential oil component of composition can be from about 0.001 wt % to about 1 wt % of the composition, and in some embodiments, about 0.065 wt % of the composition. As used herein, an "essential oil" is a concentrated, hydrophobic liquid containing volatile aroma compounds from plants and does not include vitamin E oil or an "oil" for the oil component as earlier described. Essential oils are derived from various sections of plants. An essential oil is "essential" in the sense that it carries a distinctive scent, or essence, of the plant. Essential oils are also known as volatile oils, ethereal oils or aetherolea, or simply as the "oil of" the plant from which they were extracted.

Examples of essential oils include agar oil, ajwain oil, allspice, almond, angelica oil, anise oil, asafoetida, balsam oil, basil, bay leaf, bayberry, bergamot oil, black pepper, buchu oil, birch, camphor, caraway, cardamon, carrot seed, cassia, cedarwood, celery, chamomile, calamus root, cinnamon, cistus, citronella oil, clary, clove, coffee, coriander, costmary oil, costus root, cranberry, cubeb, cumin, cypress, cypriol, curry leaf, davana oil, dill, elecampane, elemi, eucalyptus, fennel, fenugreek, fir, frankincense, galangal, galbanum, geranium, ginger, goldenrod, grapefruit, henna, helichrysum, hops, horseradish, hyssop, Idaho tansy, jasmine, juniper, juniper berry, laurel, lavender, ledum oil, lemon oil, lemongrass, lime, *Litsea cubea* oil, mandarin, manuka, marjoram, melaleuca, melissa oil, mint, mountain savory, mugwort oil, mustard oil, myrrh, myrtle, neem tree oil, neroli, niaouli, nutmeg, onion, orange, oregano, orris oil, palo santo, palma rosa, parsley, parsley seed, patchouli, perilla, pennyroyal, peppermint, petitgrain, pine, ravensara, red cedar, chamomile, rose, rosehip, rosemary, rosewood, rue, sage, sandalwood, sassafras, savory, schisandra, sea buckthorn, spearmint, spikenard, spruce, St. Johns wort, star anise, styrax, tagetes, tangerine, tarragon, tea tree, thyme, tolu balsam, tsuga, turmeric, valerian, vanilla, vetiver oil, western red cedar, wintergreen, witch hazel, wormwood, yarrow, ylang-ylang, and zedoary.

Essential oils for general skincare can include, but are not limited to, lavender, rose, rosemary camphor, cypress, chamomile, rosemary, rosewood, and geranium. Essential oils for cleansing skin can include, but are not limited to, basil, juniper, lemon, lemongrass, niaouli, rosemary, and peppermint. Essential oils for use as a skin toner can include, but are not limited to, calendula, lemongrass, chamomile, lavender, neroli, orange, rose, rosemary, frankincense, petitgrain, and lemon. Essential oils for combination skin can include, but are not limited to, geranium, neroli, rosemary, rosewood, and ylang-ylang. Essential oils for normal skin can include, but are not limited to, angelica, chamomile, cedarwood, geranium, jasmine, lavender, neroli, rose, rosemary, rosewood, and ylang-ylang. Essential oils for oily skin can include, but are not limited to, chamomile, cedarwood, geranium, clary, lavender, ylang-ylang, lemon, peppermint, niaouli, cajeput, cypress, calendula, frankincense, patchouli, sandalwood, juniper, melissa, yarrow, coriander, petitgrain, lime, grapefruit, thyme, rose and rosemary. Essential oils for sensitive skin can include, but are not limited to, chamomile, rose, palma rosa, helichrysum, neroli, rosewood, carrot, angelica, jasmine, neroli, rosemary and yarrow.

Essential oils for treating dry skin can include, but are not limited to, carrot seed, cedarwood, chamomile, clary, jasmine, geranium, lavender, orange, palma rosa, rose, rosewood, neroli, petitgrain, mandarin, vetiver, rosemary, sandalwood, and ylang-ylang. Essential oils for treating chapped or cracked skin can include, but are not limited to, calendula, myrrh, patchouli, rosemary, sandalwood, vetiver, cajeput, chamomile, and lavender. Essential oils for treating dry and devitalized skin can include, but are not limited to, eucalyptus, myrtle, neroli, basil, juniper, lemon, lemongrass, niaouli, peppermint, pine, orange, oregano, rosemary, spearmint, geranium, and grapefruit. Essential oils for hydrating the skin can include, but are not limited to, palma rosa, orange, mandarin, neroli, tangerine, rose and rosemary. Essential oils for caring for mature skin and reducing the appearance of wrinkles can include, but are not limited to, carrot seed, elemi, cistus, frankincense, galbanum, fennel, geranium, myrrh, patchouli, rose, clary, rosemary, rosewood, sage, cypress, fennel, lavender, neroli, sea buckthorn, and rosehip. Essential oils for reducing puffiness of skin can include, but are not limited to, oregano, marjoram, cypress, peppermint, rosemary, fennel, celery, clary sage, and chamomile.

Essential oils for treating acne (e.g., pores, pimples, blemishes) can include, but are not limited to, clary, coriander, peppermint, lemongrass, tea tree, lime, manuka, helichrysum, grapefruit, lavender, thyme, rose, geranium, petitgrain, grapefruit, sandalwood, vetiver, mint, basil, chamomile, cedar-wood, rosemary, rosewood, palma rosa, thyme, cajeput, niaouli, yarrow, myrtle, thyme, and oregano. Essential oils for treating skin infections can include, but are not limited to, chamomile, manuka, eucalyptus, lavender, myrrh, rosemary, spikenard, tea tree, thyme linalool, calendula, palma rosa, niaouli, laurel, myrtle, and rosewood. Essential oils for treating itching and inflammation can include, but are not limited to, helichrysum, St. Johns wort, carrot seed, cistus, clary, galbanum, jasmine, lavender, myrrh, myrtle, peppermint, rosewood, rosemary, angelica, yarrow, and witch hazel.

Essential oils for promoting skin regeneration can include, but are not limited to, frankincense, lavender, neroli, patchouli, rose, rosemary, sandalwood, tea tree, helichrysum, elemi, vetiver, spikenard, caraway, palma rosa, sage, clary, lavender, galbanum, myrrh, myrtle, calendula, carrot seed, and cistus. Essential oils for revitalizing the basal layer of skin cells can include, but are not limited to, carrot seed, rosewood, rosemary, niaouli, tea tree, orange, and calendula. Essential oils for reducing rosacea can include, but are not limited to, chamomile, helichrysum, rosemary, and rosewood. Essential oils for treating eczema can include, but are not limited to, calendula, chamomile, cranberry seed, helichrysum, lavender, bergamot, carrot seed, cedarwood, juniper, myrrh, palma rosa, patchouli, rosemary, sandalwood, tea tree, yarrow, and ylang-ylang. Essential oils for treating psoriasis can include, but are not limited to, bergamot, helichrysum, calendula, cajeput, carrot seed, chamomile, cranberry seed, lavender, juniper, rosemary, sandalwood, and tea tree. Essential oils for reducing the appearance of scars can include, but are not limited to, helichrysum, carrot seed, lavender, petitgrain, rosemary, and galbanum. Essential oils for treating perniosis, or chilblains, can include, but are not limited to, black pepper, cinnamon leaf, clove, ginger, rosemary, and lavender. Essential oils for treating couperose can include, but are not limited to, calendula, lemon, helichrysum, cypress, rose, lavender, neroli, parsley, chamomile, rosemary, and geranium.

In some embodiments, the essential oil component can be any of the above-mentioned essential oils or mixture thereof. In some embodiments, the essential oil component can be calendula, cedar, chamomiles, clove, cypress, geranium, jasmine, lavender, lemongrass, orange blossom, rose, rosemary, rosewood, peppermint, sandalwood, thyme, turmeric, or a mixture thereof.

In some embodiments, the essential oil component is rosemary oil. Rosemary oil may be extracted from Rosemary herb by steam distillation. The main chemical components of rosemary oil are a-pinene, borneol, b-pinene, camphor, bornyl acetate, camphene, 1,8-cineole and limonene. Rosemary oil is used for its many therapeutic properties such as analgesic, antidepressant, astringent, carminative, cephalic, cordial, digestive, diuretic, emmenagogue, hepatic, hypertensive, nervine, rubefacient, stimulant, sudorific and tonic properties.

In some embodiments, the composition contains all organic components.

In some embodiments, the composition is a topical lubricant. In some embodiments, the composition may be applied to the skin in adequate quantity and in the manner conventional in the relevant field. Such topical compositions are useful for treating the skin and skin diseases which include, but are not limited to, chafing, rashes, blisters, acne, fungal infections, bacterial infections, burns, insect bites, microbial infections, sunburn, scabies, scrapes, cuts and combinations thereof. In some embodiments, the topical lubricant is a moisturizer, such as a skin or hair moisturizer.

In some embodiments, the composition is a semi-solid at room temperature, or at a temperature of about 72° F. Suitable semi-solid mixtures of the compositions may include, for example, gels, lotions, pastes, balms, creams and ointments.

In some embodiments, the composition has a viscosity of from about 2,000 cP to about 2,500,000 cP, from about 10,000 cP to about 2,000,000 cP, from about 25,000 cP to about 1,000,000 cP, from about 50,000 cP to about 750,000 cP, from about 100,000 cP to about 500,000 cP, or from about 200,000 cP to about 400,000 cP. In some embodiments, the composition can also be free of hydrogenated components.

According to some exemplary embodiments of the present invention, the composition includes from about 15 wt % to about 40 wt % of a wax, from about 60 wt % to about 85 wt % of an oil, from about 0.01 wt % to about 10 wt % of vitamin E oil, and from about 0.001 wt % to about 1 wt % of an essential oil, and is free of petroleum-based components. In some embodiments, the sum of the wax, the oil, the vitamin E oil, and the essential oil in the composition is about 100 wt %.

In some embodiments, the composition includes about 24.9 wt % of a wax, about 74.9 wt % of an oil, about 0.135 wt % of vitamin E oil and about 0.065 wt % of the essential oil. In some embodiments, the wax can be beeswax, the oil can be soybean oil, and the essential oil can be rosemary oil.

In some embodiments, the composition is made substantially entirely of only from about 15 wt % to about 40 wt % beeswax, from about 60 wt % to about 85 wt % soybean oil, from about 0.01 wt % to about 10 wt % vitamin E oil, and from about 0.001 wt % to about 1 wt % of an essential oil. In such embodiments, the sum of the wax, the oil, the vitamin E oil, and the essential oil in the composition is about 100 wt %. The composition is free of petroleum-based components, can be a semi-solid at a temperature of about 72° F., can have a viscosity of from about 2,000 cP to about 2,500,000 cP, and can also be free of hydrogenated components, as noted above. The beeswax can have a melting point of from about 130° F. to about 160° F., as noted above.

In other embodiments, further additional components suitable for inclusion in the compositions of the present invention will be familiar to the ordinarily skilled artisan.

Process of Preparing

Exemplary processes for preparing substantially anonaqueous, aerated compositions, including but not limited to the exemplary compositions described above, will now be described with reference to FIG. 1. As shown in FIG. 1, an exemplary process 100 for preparing a substantially non-aqueous, aerated composition includes steps 110, 120, 130, and 140. In step 110, component ingredients are melted together to form a mixture. The temperature for the melting can be from about 130° F. to about 180° F., from about 140° F. to about 170° F., or from about 150° F. to about 160° F., for example. The components can be melted together in a double boiler or a wax-melter, for example, or any other suitable appliance known in the art.

In step 120 of exemplary process 100, the mixture is poured into a cooling vessel where it is cooled completely to room temperature to form hardened matter (e.g., one or more hardened blocks of the cooled mixture). In some embodiments, the hardened matter shrinks and pulls away from the sides of the cooling vessel. In some embodiments, the hardened matter increases in density. In step 130, the hardened matter is blended with a mixer to form a flowable mixture that can be creamy in texture, and in step 140, the flowable mixture is forced through a sieve to form the aerated composition. In some embodiments, the flowable mixture has a particulate size of less than about one inch in diameter. In some embodiments, the sieve can include a mesh screen and/or a perforated metal plate. In some embodiments, the sieve is a mesh screen. In some embodiments, the sieve is a perforated metal plate, i.e., a metal plate with holes. In some embodiments, the holes are laser drilled. In some embodiments, the sieve has a sieve hole size of from about ½ inch to about 1/200 inch, from about ⅓ inch to about 1/170 inch, from about ¼ inch to about 1/128 inch, from about ⅛ inch to about 1/64 inch, or from about 1/16 inch to about 1/32 inch. In some embodiments, the sieve hole size is about 1/30 inch (or about 846 microns). In some embodiments, the sieve has a sieve hole size of about 0.033 inch, about 0.015 inch, about 0.009 inch, or about 0.006 inch. In some embodiments, the amount of pressure used to force the flowable mixture through a sieve is from about 60 to about 150 psi of pneumatic pressure, from about 70 to about 130 psi of pneumatic pressure, from about 85 to about 120 psi of pneumatic pressure, or from about 100 to about 110 psi of pneumatic pressure.

In some embodiments, the resulting the aerated composition can have a viscosity of from about 2,000 cP to about 2,500,000 cP. In some embodiments, the aerated composition has a viscosity of about 250,000 cP. In some embodiments, the volume of the aerated composition increases by about 2% to about 10%, by about 4% to about 6%. In some embodiments, the volume of the aerated composition increases by about 4.17%. In some embodiments, the aerated composition has a creamy and smooth, airy texture. In some embodiments, the aerated composition has a particulate size of less than the size of the sieve hole size. In some embodiments, the aerated composition has a particulate size of less than about 1/30$^{th}$ of an inch.

In some embodiments, the wax is from about 15 wt % to about 40 wt %, and wherein the oil is from about 60 wt % to about 85 wt %. In some embodiments, the wax is beeswax and the oil is soybean oil. In some embodiments, all or a portion of at least one of the soybean oil or the beeswax is substituted by one or more components selected from the group consisting of carnauba wax, coconut oil, olive oil, soy wax and vegetable oil.

In, some embodiments, in step 110, the component ingredients melted together include the wax, the oil, and additionally vitamin E oil and/or aloe vera extract. In some embodiments, an amount of the vitamin E oil and/or aloe vera extract can be from about 0.01 wt % to about 10 wt % of the composition. In some embodiments, the component ingredients farther included an essential oil, and in some embodiments, an amount of the essential oil is from about 0.001 wt % to about 1 wt % of the composition. In some embodiments, the essential oil component can be one or more of the essential oils described above, the wax component can be one or more of the exemplary waxes described above, and the oil component can be one or more of the oils described above.

In some embodiments, process 100 only includes steps 110, 120, 130 and 140 to form the aerated composition. For example, step 110 can involve melting together (a) from about 15 wt % to about 40 wt % of a wax which is animal tallow, bayberry wax, beeswax, candelilla wax, carnauba wax, grapefruit wax, montan wax, orange peel wax, rice bran wax, sumac wax, sunflower wax, soy wax, or a mixture thereof, (b) from about 60 wt % to about 85 wt % of an oil which is almond oil, babassu kernel oil, carrot seed oil, cashew oil, castor oil, coconut oil, cottonseed oil, corn oil, grape seed oil, hazelnut oil, linseed oil, macadamia oil, mongongo nut oil, olive oil, palm oil, palm kernel oil, peanut oil, pecan oil, pine nut oil, pistachio oil, pumpkin seed oil, rapeseed oil, safflower oil, sesame oil, soybean oil, sunflower oil, vegetable oil, walnut oil, or a mixture thereof, (c) optionally, from about 0.01 wt % to about 10 wt % vitamin E oil, and (d) optionally, from about 0.001 wt % to about 1 wt % of an essential oil. The resulting aerated composition after subsequent steps 120, 130, and 140 can have a viscosity of from about 2,000 cP to about 2,500,000 cP, and can be free of petroleum-based components and hydrogenated components.

It will be readily apparent to one of ordinary skill in the relevant arts that other suitable modifications and adaptations to the methods and applications described herein are obvious and may be made without departing from the scope of the invention or any embodiment thereof. Having now described the present invention in detail, the same will be more clearly understood by reference to the following example, which is included herewith for purposes of illustration only and is not intended to be limiting of the invention.

EXAMPLE

This Example describes an exemplary process for producing a substantially a non-aqueous, aerated composition including beeswax, soybean oil, vitamin E oil and rosemary oil. The composition is prepared as follows: beeswax (24.9% wt), soybean oil (74.9% wt), vitamin E oil (0.13% wt) and rosemary oil (0.065% wt) are melted together in a 70 gallon commercial grade wax-melter at about 170° F. The batch of these ingredients weighs about 393 lbs with a volume of about 48 gallons. The mixture is blended by stirring to ensure substantial uniformity and homogeneous distribution of the component ingredients. The mixture is then transferred to a cooling vessel to allow the mixture to solidify and cool to room temperature overnight. The resulting solidified mixture forms blocks of hardened matter which are transferred from the cooling vessel to a large mixer (100 qt capacity), in which the blocks are blended into a semi-solid mixture having a creamy texture while still containing some particulates of the hardened matter. The size of the particulates in the resulting blended mixture is less than about one inch in diameter.

The mixture is then transferred from the large mixer to a piston filler machine (custom manufactured by Accutek Packaging Equipment Companies, Inc. of Vista, Calif.). In particular, the mixture is forced (using 85-120 psi of pneumatic pressure) through a sieve to break up the particulates of the hardened matter and create a smooth airy texture. The sieve is a metal plate with holes of about 1/30$^{th}$ of an inch in diameter. This process reduces the hardened matter particulates to less than the size of the sieve plate holes.

The viscosity of the resulting aerated composition is 250,000 cf., and the size of any particulates in the composition is less than about $1/30^{th}$ of an inch. The volume of the batch is now about 50 gallons. The particulates are substantially homogenously dispersed in the composition. The resulting composition has an increased volume of about 4.17%. The resulting composition is free of petroleum-based components, does not contain hydrogenated components, and has a consistency that is similar to petroleum jelly. The resulting aerated composition can be used as a replacement lubricant for applications in which petroleum jelly may be used.

All of the various embodiments or options described herein can be combined in any and all variations. While the invention has been particularly shown and described with reference to some embodiments thereof, it will be understood by those skilled in the art that they have been presented by way of example only, and not limitation, and various changes in form and details can be made therein without departing from the spirit and scope of the invention. Thus, the breadth and scope of the present invention should not be limited by any of the above described exemplary embodiments, but should be defined only in accordance with the following claims and their equivalents.

What is claimed is:

1. A process for the preparation of a substantially non-aqueous, aerated composition, comprising:
   i. melting together components including (a) a wax and (b) an oil to form a mixture;
   ii. pouring the mixture into a cooling vessel where it is cooled completely to room temperature to form one or more solid blocks;
   iii. blending the one or more solid blocks with a mixer to change the one or more solid blocks from solid blocks to a flowable mixture; and
   iv. introducing air into the flowable mixture by forcing the flowable mixture through a sieve to form the aerated composition.

2. The process according to claim 1, wherein the wax comprises from about 15 wt % to about 40 wt %, and wherein the oil comprises from about 60 wt % to about 85 wt %.

3. The process according to claim 1, wherein (a) the wax is beeswax and (b) the oil is soybean oil.

4. The process according to claim 3, wherein all or a portion of at least one of the soybean oil and the beeswax is substituted by one or more components selected from the group consisting of coconut oil, olive oil, soy wax and vegetable oil.

5. The process according to claim 2, wherein (i) melting together comprises melting components (a) and (b) together with (c) from about 0.01 wt % to about 10 wt % of one or more of vitamin E oil and aloe vera extract.

6. The process according to claim 5, wherein (i) melting together comprises melting components (a), (b) and (c) together with (d) from about 0.001 wt % to about 1 wt % of an essential oil.

7. The process according to claim 6, wherein (d) the essential oil is selected from the group consisting of calendula, cedar, chamomiles, clove, cypress, geranium, jasmine, lavender, lemongrass, orange blossom, rose, rosemary, rosewood, peppermint, sandalwood, thyme, turmeric, and mixtures thereof.

8. The process according to claim 1, wherein (a) the wax is selected from the group consisting of animal tallow, bayberry wax, beeswax, grapefruit wax, orange peel wax, palm wax, rice bran wax, sumac wax, sunflower wax, soy wax, and mixtures thereof.

9. The process according to claim 1, wherein (b) the oil is selected from the group consisting of almond oil, babassu kernel oil, carrot seed oil, cashew oil, coconut oil, cottonseed oil, corn oil, grape seed oil, hazelnut oil, linseed oil, macadamia oil, mongongo nut oil, olive oil, palm oil, palm kernel oil, peanut oil, pecan oil, pine nut oil, pistachio oil, pumpkin seed oil, rapeseed oil, safflower oil, sesame oil, soybean oil, sunflower oil, vegetable oil, walnut oil, and mixtures thereof.

10. The process according to claim 1, wherein (i) melting together comprises melting together components (a) and (b) at a temperature of from about 140° F. to about 170° F.

11. The process according to claim 1, wherein the sieve has a sieve hole size of from about ¼ inch to about 1/128 inch.

12. The process according to claim 1, wherein the aerated composition has a viscosity of from about 2,000 cP to about 2,500,000 cP.

13. The process according to claim 1, wherein the aerated composition is a topical lubricant.

14. The process according to claim 1, wherein the aerated composition is free of petroleum-based components.

15. A composition prepared by the process of claim 1.

16. A process for the preparation of a substantially non-aqueous, aerated composition, consisting essentially of:
   i. melting together
      1. from about 15 wt % to about 40 wt % of a wax selected from the group consisting of animal tallow, bayberry wax, beeswax, grapefruit wax, orange peel wax, rice bran wax, sumac wax, sunflower wax, soy wax, and mixtures thereof;
      2. from about 60 wt % to about 85 wt % of an oil selected from the group consisting of almond oil, babassu kernel oil, carrot seed oil, cashew oil, coconut oil, cottonseed oil, corn oil, grape seed oil, hazelnut oil, linseed oil, macadamia oil, mongongo nut oil, olive oil, palm oil, palm kernel oil, peanut oil, pecan oil, pine nut oil, pistachio oil, pumpkin seed oil, rapeseed oil, safflower oil, sesame oil, soybean oil, sunflower oil, vegetable oil, walnut oil, and mixtures thereof;
      3. optionally, from about 0.01 wt % to about 10 wt % vitamin E oil; and
      4. optionally, from about 0.001 wt % to about 1 wt % of an essential oil;
   ii. pouring the mixture into a cooling vessel where it is cooled completely to room temperature to form hardened matter;
   iii. blending the hardened matter with a mixer to form a flowable mixture; and
   iv. forcing the flowable mixture through a sieve to form the aerated composition.

17. The process according to claim 16, wherein (i) melting together comprises melting components (a) and (b) together with (c) from about 0.01 wt % to about 10 wt % vitamin E oil.

18. The process according to claim 17, wherein (i) melting together comprises melting components (a), (b) and (c) together with (d) from about 0.001 wt % to about 1 wt % of an essential oil.

19. The process according to claim 18, wherein the essential oil is selected from the group consisting of calendula, cedar, chamomiles, clove, cypress, geranium, jasmine, lavender, lemongrass, orange blossom, rose, rosemary, rosewood, peppermint, sandalwood, thyme, turmeric, and mixtures thereof.

20. The process according to claim 18, wherein the aerated composition has a viscosity of from about 2,000 cP to about 2,500,000 cP, wherein the aerated composition is free of petroleum-based components or hydrogenated components.

21. The process according to claim 1, wherein the volume of the flowable mixture is less than the volume of the aerated composition.

22. The process according to claim 1, wherein the sieve is a perforated plate.

23. The process according to claim 1, wherein blending the one or more solid blocks increases the viscosity of the one or more solid blocks to form the flowable mixture, and
   wherein forcing the flowable mixture through a sieve increases the viscosity of the flowable mixture to form the aerated composition.

24. The process according to claim 1, wherein the composition of the flowable mixture is the same as the composition of the aerated composition.

* * * * *